United States Patent
Nath et al.

(10) Patent No.: US 10,737,261 B1
(45) Date of Patent: Aug. 11, 2020

(54) REVERSIBLY BONDED DEVICES AND METHODS OF MAKING AND USING THE SAME

(71) Applicant: Los Alamos National Security, LLC, Los Alamos, NM (US)

(72) Inventors: Pulak Nath, Los Alamos, NM (US); Jen-Huang Huang, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 61 days.

(21) Appl. No.: 15/719,187

(22) Filed: Sep. 28, 2017

Related U.S. Application Data

(60) Provisional application No. 62/401,663, filed on Sep. 29, 2016.

(51) Int. Cl.
*B01L 3/00* (2006.01)
*G01N 33/50* (2006.01)

(52) U.S. Cl.
CPC .......... *B01L 3/502* (2013.01); *G01N 33/5005* (2013.01); *B01L 2200/12* (2013.01); *B01L 2300/0681* (2013.01); *B01L 2300/0816* (2013.01); *B01L 2300/0887* (2013.01)

(58) Field of Classification Search
CPC ................ B01L 3/502; B01L 2200/12; B01L 2300/0681; B01L 2300/0816; B01L 2300/0887; G01N 33/5005
See application file for complete search history.

(56) References Cited

U.S. PATENT DOCUMENTS

| | | | |
|---|---|---|---|
| 6,485,625 B1 * | 11/2002 | Simpson | B01J 19/0093 204/450 |
| 2002/0172621 A1 * | 11/2002 | Barbera-Guillem | B01L 3/50853 422/503 |
| 2010/0243078 A1 * | 9/2010 | Yoo | F16K 99/0001 137/468 |

* cited by examiner

*Primary Examiner* — Michael L Hobbs
(74) *Attorney, Agent, or Firm* — Klarquist Sparkman, LLP

(57) ABSTRACT

The present disclosure concerns embodiments of reversibly bonded devices that comprise a reversible bonding component. The reversible bonding component is able to exhibit strong adhesive properties so as to couple device components, but upon exposure to an energy source, the strong adhesive properties are weakened. By weakening the adhesive strength of the reversible bonding component, the device can be deconstructed to access internal biological samples for analysis and characterization.

15 Claims, 12 Drawing Sheets

REVERSIBLY BONDED DEVICES AND METHODS OF MAKING AND USING THE SAME

CROSS REFERENCE TO RELATED APPLICATION

This application claims the benefit of U.S. Provisional Patent Application No. 62/401,663, filed on Sep. 29, 2016, which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

The present disclosure concerns embodiments of reversibly bonded components and devices for use in fluidic applications. Methods of making such components and devices also are disclosed.

BACKGROUND

Using fluidic devices in biological applications (e.g., organ-on-a-chip technologies, bioreactor technologies, and the like) has become increasingly popular due to the ability to analyze biological systems and functions in vitro. In particular, organ-on-a-chip technologies have advanced considerably in the past decade; however, understanding of biological scaling laws and how they apply to multiple, coupled organ devices has been largely ignored. To replicate human physiology and drug response with interconnected human organs-on-a-chip and larger human-like organ devices, each construct should have the correct relative size. Appropriate scaling of devices therefore is an important factor that must be carefully controlled; thus, devices must retain functional integrity both on small and large scales. Controlling device integrity for large-scale devices can be difficult when conventional construction techniques are utilized, such as using gaskets and/or external hardware to couple components of the device. Another factor that is important when using fluidic devices in biological applications is the ability to have ready access to samples (e.g., cell cultures, cell culture media, and the like) without destroying device or sample integrity. Conventional methods of adhering device components together typically involve using permanent adhesive methods that then require breaking the device and/or components of the device to access internal samples for characterization purposes. Destroying the device and/or components of the device to access internal samples often results in destroying sample integrity and further results in increased production costs as components of the device must be replaced for further use. As such, there exists a need in the art for adhesive components that can facilitate device construction but that also facilitate device deconstruction to allow ready access to internal samples without affecting device or sample integrity.

SUMMARY

Disclosed herein are embodiments of reversibly bonded devices. In some embodiments, the devices can comprise a first device component; a second device component; a reversible bonding component coupled to the first device component, the second device component, or both, wherein the first device component and the second device component are reversibly coupled by the reversible bonding component. In some embodiments, the reversibly bonded device can further comprise a biological sample contained within the reversible bonded device.

Also disclosed herein are embodiments of a reversibly bonded device that comprises a first transparent substrate; a second transparent substrate; a membrane positioned between the first transparent substrate and the second transparent substrate; a membrane holder component coupled to the membrane and positioned between the first transparent substrate and the second transparent substrate; a first UV tape layer adhered to a first surface of the membrane holder component and a surface of the first transparent substrate; and a second UV tape layer adhered to a second surface of the membrane holder component and a surface of the second transparent substrate.

Also disclosed herein are embodiments of a method of making a reversibly bonded device, comprising: adhering a reversible bonding component to a surface of a first device component; adhering the reversible bonding component to a surface of a second device component; and coupling the first device component to the second device component through the reversible bonding component.

Also disclosed herein are embodiments of a method of using a reversibly bonded device, comprising introducing a biological sample into the reversibly bonded device or growing a biological sample in the reversibly bonded device; exposing the reversibly bonded device to a light source. In some embodiments, the method can further comprise deconstructing the reversibly bonded device to access the biological sample for analysis.

The foregoing and other objects, features, and advantages of the present disclosure will become more apparent from the following detailed description, which proceeds with reference to the accompanying figures.

BRIEF DESCRIPTION OF THE DRAWINGS

FIG. 8A illustrates the constructed device and FIG. 8B is an exploded perspective view of the device of FIG. 8A.

DETAILED DESCRIPTION

I. Explanation of Terms

Figure 1:
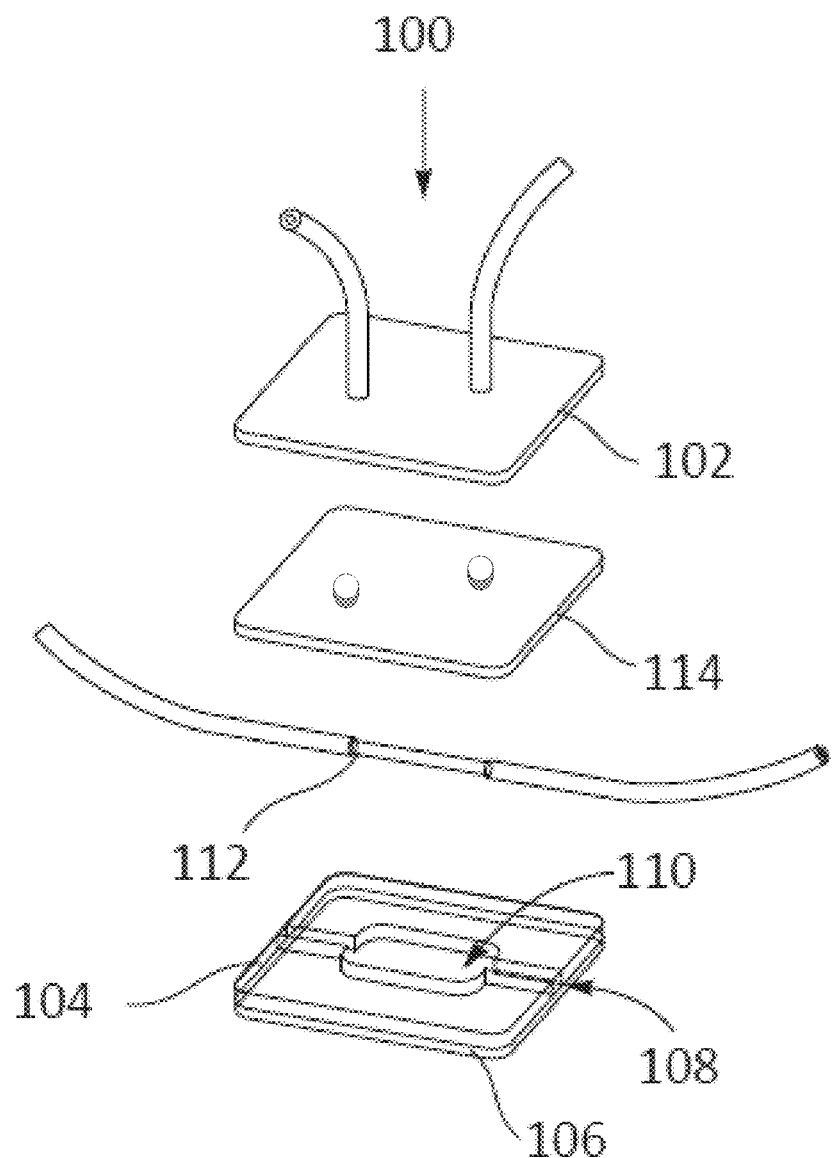
FIG. 1 is an exploded perspective view of a representative fluidic device that can be constructed using a reversible bonding component as described herein.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided:

Adhesive Transfer Tape: A tape, film, or paper (or other similar structure) that is composed solely of an adhesive layer. In some embodiments, adhesive transfer tapes do not include a carrier layer.

Adhesive UV Tape: A tape, film, or paper (or other similar structure) that comprises at least one adhesive surface wherein the adhesion strength of the tape, film, or paper can be modified with light, such as ultraviolet or visible light, such that the adhesion strength is reduced upon exposure to such light. In some embodiments, the adhesive UV tape can comprise one adhesive layer and a carrier layer. In yet additional embodiments, the adhesive UV tape can comprise two adhesive layers. The terms "adhesive UV tape" and "adhesive UV film" can be used interchangeably herein.

Bonded: This term refers to two or more device components or other components described herein that are physically joined together (directly or indirectly).

Device Component: In some embodiments, a device component can include any components described herein that are used to construct a completed device. Exemplary device components include, but are not limited to, substrates, membranes, membrane holder components, hollow tubes, valves, pumps, and the like. In some embodiments, individual devices can constitute device components when they are used to construct a separate singular device. Examples of such device components include, but are not limited to, alveolar devices, bronchiolar devices, fluid management devices, and the like.

Patterned Reversible Bonding Component: A reversible bonding component that has been patterned to match one or more patterns of a device component. In some embodiments, a patterned reversible bonding component comprises one or more patterns created by penetrating the depth/thickness of the reversible bonding component. In yet additional embodiments, a patterned reversible bonding component can be formed by depositing a solution comprising a reversible bonding component onto a substrate or device component in a pattern. Patterns can include, but are not limited to, fluidic channels, inlets, outlets, or the like that are cut through the reversible bonding component.

Reversibly Bonded Device: A device comprising a reversible bonding component, wherein the device is capable of being constructed and/or deconstructed (e.g., two or more device components can be physically disassembled to provide each separate device component) due to the reversible bonding properties of the reversible bonding component.

Reversible Bonding/Reversibly Bonded: These terms refer to the ability to physically join two or more device components together using a reversible bonding component and then separate the two or more device components by modifying (e.g., reducing) the adhesive strength of the reversible bonding component.

Transparent substrate: A substrate made of a material that permits light, such as visible or UV light, to pass through the substrate.

II. Introduction

Devices used in fluidic analysis often comprise a plurality of components that are fluidly coupled together. In particular, such devices often comprise plural substrates that are stacked together, with one or more substrates comprising fluidly coupled fluidic channels that communicate fluids through the different substrates of the device. Such devices can be useful in biological and non-biological applications; however, conventional devices typically are constructed by permanently adhering the various different substrates or other components of the device together and/or by using external hardware to hold the substrates or other components together. Each of these methods has associated drawbacks/limitations. In biological applications, for example, most of the reactions and interactions that are being analyzed occur within internal components of the microfluidic devices. As such, information to be measured and/or assessed from using such devices must be obtained by characterizing the internal sample undergoing the changes within the device. This is difficult with permanently-adhered microfluidic devices because one cannot easily access the sample to characterize it. In devices constructed by permanently adhering substrates, one must physically break the device to gain access to the sample, which often results in damaging other device components, damaging the sample itself, and increasing production costs. Devices that utilize external hardware, such as clamps, gaskets, screws, or the like, to hold device components together with pressure also introduce undesirable drawbacks as they are prone to leakage and are not suitable for large-scale analysis. All of these drawbacks also can deleteriously affect samples within the device and prevent or at least inhibit characterization of such samples.

The present inventors have developed a unique solution to the deficiencies of conventional microfluidic devices. The present disclosure describes the novel and inventive use of a reversible bonding component that provides the ability to bind various components within a fluidic device (e.g., a microfluidic device) as well as the ability to separate such components from other components within the device without damaging the device. The reversible bonding component is able to strongly adhere the device components together during use, but when analysis of internal components and/or samples is needed, its adhesive strength can be altered (e.g., decreased) to allow separation of the adhered components. As such, devices and methods of making such devices disclosed herein avoid or decrease the deleterious drawbacks discussed above. The reversible bonding component is easily applied to components of a microfluidic device as it can be applied as a simple layer onto a component or it can be patterned onto a component in a particular pattern or solely on a particular section of the component. The reversible bonding component exhibits great utility for biological applications as it provides the ability to analyze internal biological samples while maintaining device integrity and decreasing damage to or avoiding destruction of the sample itself.

III. Components and Devices

Described herein are embodiments of a reversible bonding component and use of this component in various fluidic-based devices. The reversible bonding component (referred to in some examples herein as "adhesive UV film," "adhesive UV tape," "adhesive UV composition," or similar terms) is capable of exhibiting different strengths of adhesion. For example, it can exhibit strong adhesion in its normal state and can exhibit reduced adhesion upon exposure to an energy source. In particular disclosed embodiments, the adhesion strength of the reversible bonding component can be reduced by exposing it to an energy source emitting visible and/or ultraviolet (UV) light. In particular disclosed embodiments, the energy source emits light having wavelengths ranging from 400 nm to 10 nm, or from 400 nm to greater than 320 nm, or from 400 nm to 350 nm. In some embodiments, the reversible bonding component can lose 80% to 100% (such as 80% to 98%, or 85% to 95%, or 90% to 95%) of its adhesion strength (as determined by mechanical strength testing or any other suitable method) upon exposure to UV light.

In particular disclosed embodiments, the reversible bonding component can comprise an adhesive UV film formed by, for example, an adhesive UV tape or an adhesive UV composition. Adhesive UV tapes exist commercially and can be purchased from commercial sources. Representative adhesive UV tapes include, but are not limited to, UV adhesive plastic films and antistatic UV adhesive plastic films from Ultron Systems (Moorpark, Calif.) and/or UV curable dicing tape from Semiconductor Equipment Corp (Moorpark, Calif.). Adhesive UV tapes typically are one-sided tapes; however, the present inventors are able turn commercially-available one-sided adhesive UV tapes into double-sided adhesive UV tapes using methods described herein. In yet additional embodiments, an adhesive UV composition, such as an adhesive UV paste, can be used as the reversible bonding component. Adhesive UV compositions can comprise similar UV-sensitive components as adhesive UV tapes, but are formed into a solution or paste that can be deposited in patterns using conventional deposition techniques (e.g., spin-coating, dipping, ink-jet printing, sputtering, and the like).

The reversible bonding component typically is used in combination with two or more device components such that the reversible bonding component provides a mechanism for coupling the two or more device components together. Device components that can be used in combination with the reversible bonding component include, but are not limited to, substrates, incubation chambers, tissue/cell growth components, fluid management devices, and the like. In particular disclosed embodiments, the component coupled to the reversible bonding component is transparent so as to allow light from an energy source to pass through the component and reach the reversible bonding component. In some embodiments, multiple (or all) components of the device can be transparent. In other embodiments, at least one component of the device or a portion of at least one component of the device is not transparent, for example, to maintain bonding of the component when exposed to UV light. In particular disclosed embodiments, any of the device components described in any of the following documents can be used in combination with the reversible bonding component to provide a reversibly bonded device: WO 2016/049363, entitled "BIO-ASSESSMENT DEVICE AND METHOD OF MAKING THE DEVICE," WO 2016/049365, entitled "DEVICES FOR FLUID MANAGEMENT," and U.S. patent application Ser. No. 15/488,119, entitled "MAGNETICALLY CONTROLLED VALVE AND PUMP DEVICES AND METHODS OF USING THE SAME," each of which is incorporated by reference herein.

In a representative embodiment, the reversible bonding component can be used in combination with the components of a bronchiolar device, such as the bronchiolar device 100 illustrated in FIG. 1. The bronchiolar device 100 of FIG. 1 is one that can be serially coupled to an alveolar device for use in in vitro/benchtop analysis of the biological functions of the human lung. Device 100 includes a first substrate 102, a second substrate 104, and a third substrate 106, with the second substrate being positioned between the first and third substrates, as illustrated in FIG. 1. Each of these components can be coupled together using layers of the reversible bonding component 114, with a first layer being positioned between the first substrate 102 and the second substrate 104 and a second layer (not illustrated) being positioned between the second substrate and the third substrate 106. As further shown in FIG. 1, the third substrate 106 can be fabricated to include at least one channel 108 that can be fluidly coupled with an incubation chamber 110. In some embodiments, the layers of the reversible bonding component can be patterned so that the reversible bonding component layer does not cover the channel 108 and/or the incubation chamber 110; however, patterning is not necessary as the reversible bonding component will not deleteriously affect any sample occupying these spaces. Third substrate 106 can be configured to accept a hollow tube 112, within or upon which a sample can exist or be grown.

Figure 2A:
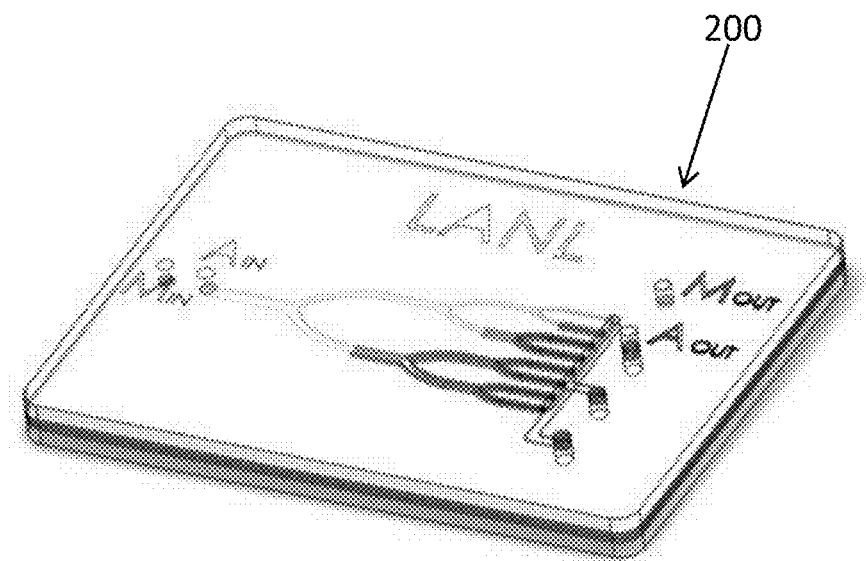
FIGS. 2A and 2B are illustrations of a reversible bonded device (FIG. 2A) and the various components of the device that can be coupled together using a reversible bonding component (FIG. 2B).
Figure 2B:
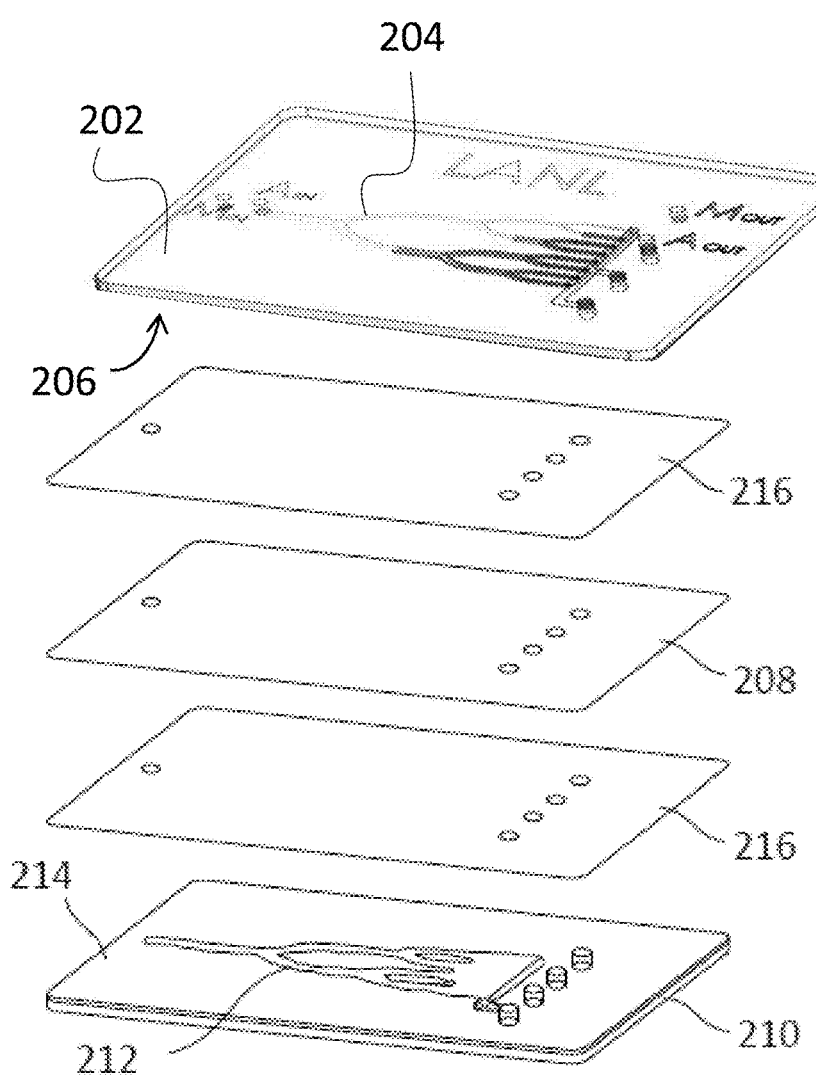

In yet another representative embodiment, the reversible bonding component can be used to couple components used in a branching bronchiolar device. An exemplary branching bronchiolar device embodiment 200 is illustrated in FIG. 2A. As illustrated in FIG. 2B, the branching bronchiolar device 200 of FIG. 2A includes a first substrate 202 comprising a plurality of channels 204 formed within the substrate that includes a branching pattern mimicking the bronchiolar geometry in a lung (such as a human lung). In particular disclosed embodiments, channels 204 can be fabricated to be open on one side, such as the underside 206 of first substrate 202 so that the channels 204 can be in fluid communication with membrane 208. Device 200 can further include a second substrate 210 that also includes a plurality of channels 212 having a similar branching pattern as the first substrate 202. A reversible bonding component 216 can be positioned between first substrate 202 and membrane 208 and also between the membrane and second substrate 210. The reversible bonding component layer can be patterned to have a similar pattern matching the patterns of first substrate 202 and/or the second substrate 210. Similar to first substrate 202, channels 212 can be open on one side, such as the top side 214, of second substrate 210 so that they can be in fluid communication with membrane 208. The reversible bonding component layer can be formed on surfaces of membrane 208, or it can be formed on the surface of first substrate 202 that is positioned to face the membrane. A second reversible bonding component layer 216 can be positioned on the surface of second substrate 210 that faces membrane 208, or it can be positioned on a surface of the membrane. As illustrated in FIG. 2B, membrane 208 can be placed between the first substrate 202 and the second substrate 210 and the reversible bonding component can thereby couple the three components together.

Figure 3:
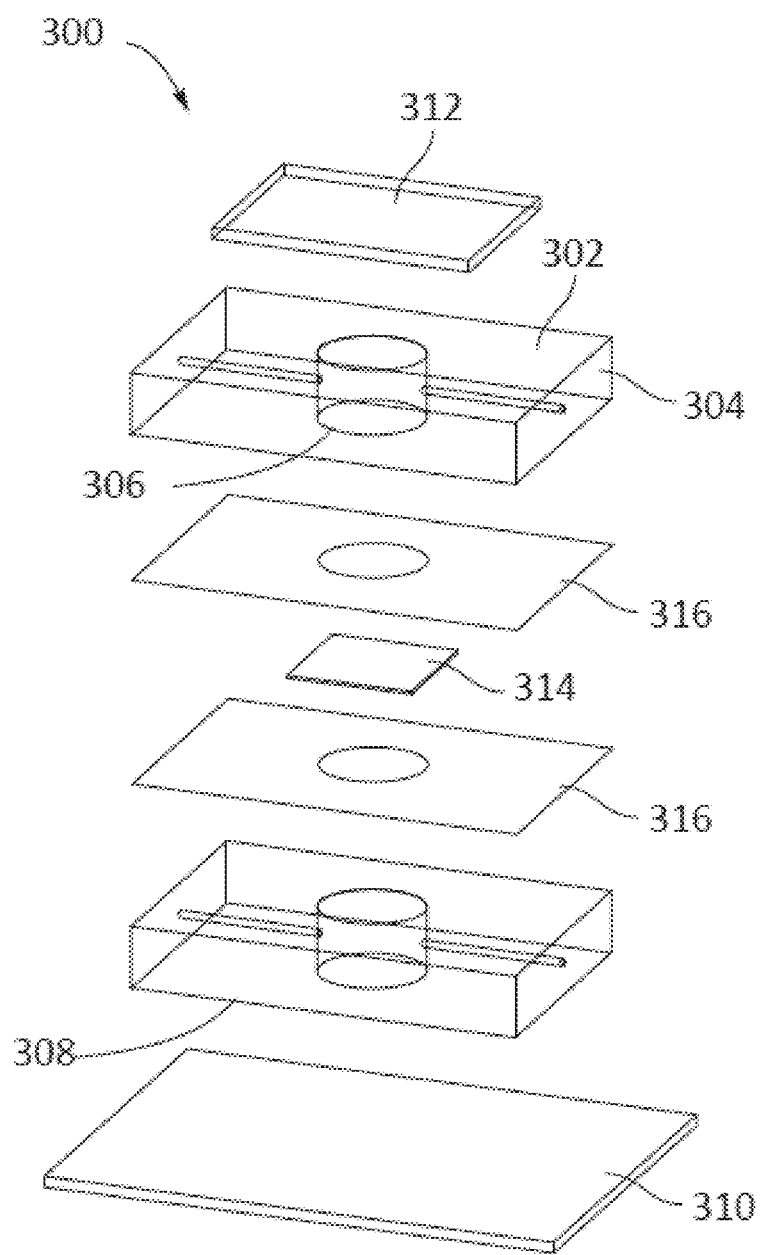
FIG. 3 is an exploded perspective view of a representative reversibly bonded device.
Figure 4:
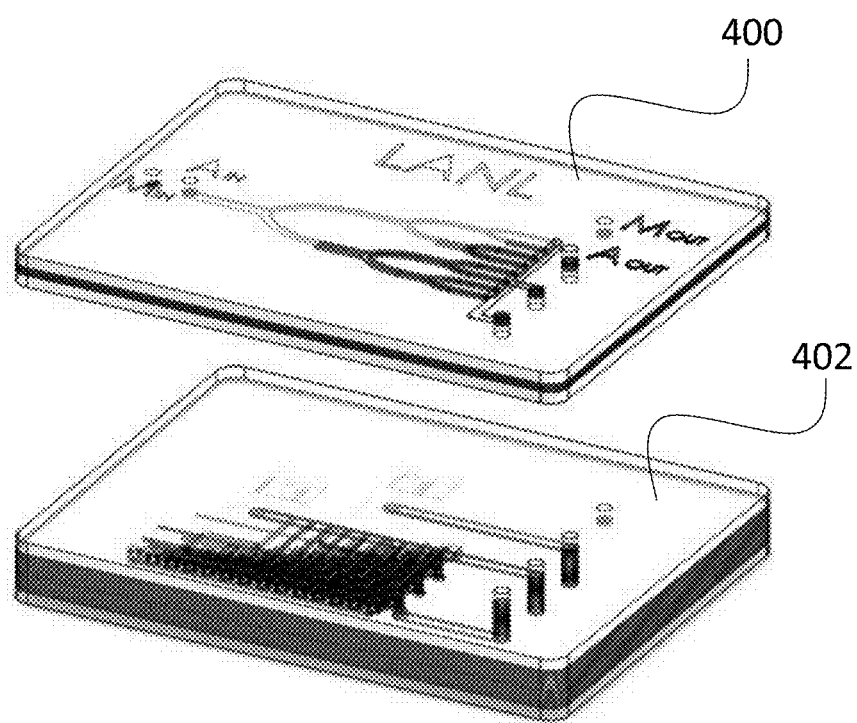
FIG. 4 is an exploded perspective view of another representative reversibly bonded device.

Yet another representative embodiment of a device that can be constructed using the reversible bonding component is an alveolar device, such as alveolar device 300 illustrated in FIG. 3. As illustrated in FIG. 3, a first substrate 302 includes channel 304 and air chamber 306 through which fluid, such as air, gas, or a combination thereof, can flow from a bronchiolar device embodiment into and out of alveolar device 300. Additional substrates, such as substrates 308, 310, and 312 can be adhered to substrate 302 (directly or indirectly) using the reversible bonding component (e.g., using multiple layers of the reversible bonding component 316). A membrane 314 also can be included, which can be adhered to substrates 302 and 308. Additionally, alveolar devices can be coupled to bronchiolar devices using the reversible bonding component. For example, the alveolar device 400 and bronchiolar device 402 illustrated in FIG. 4 can be coupled together through a reversible bonding component layer (not illustrated).

Figure 5:
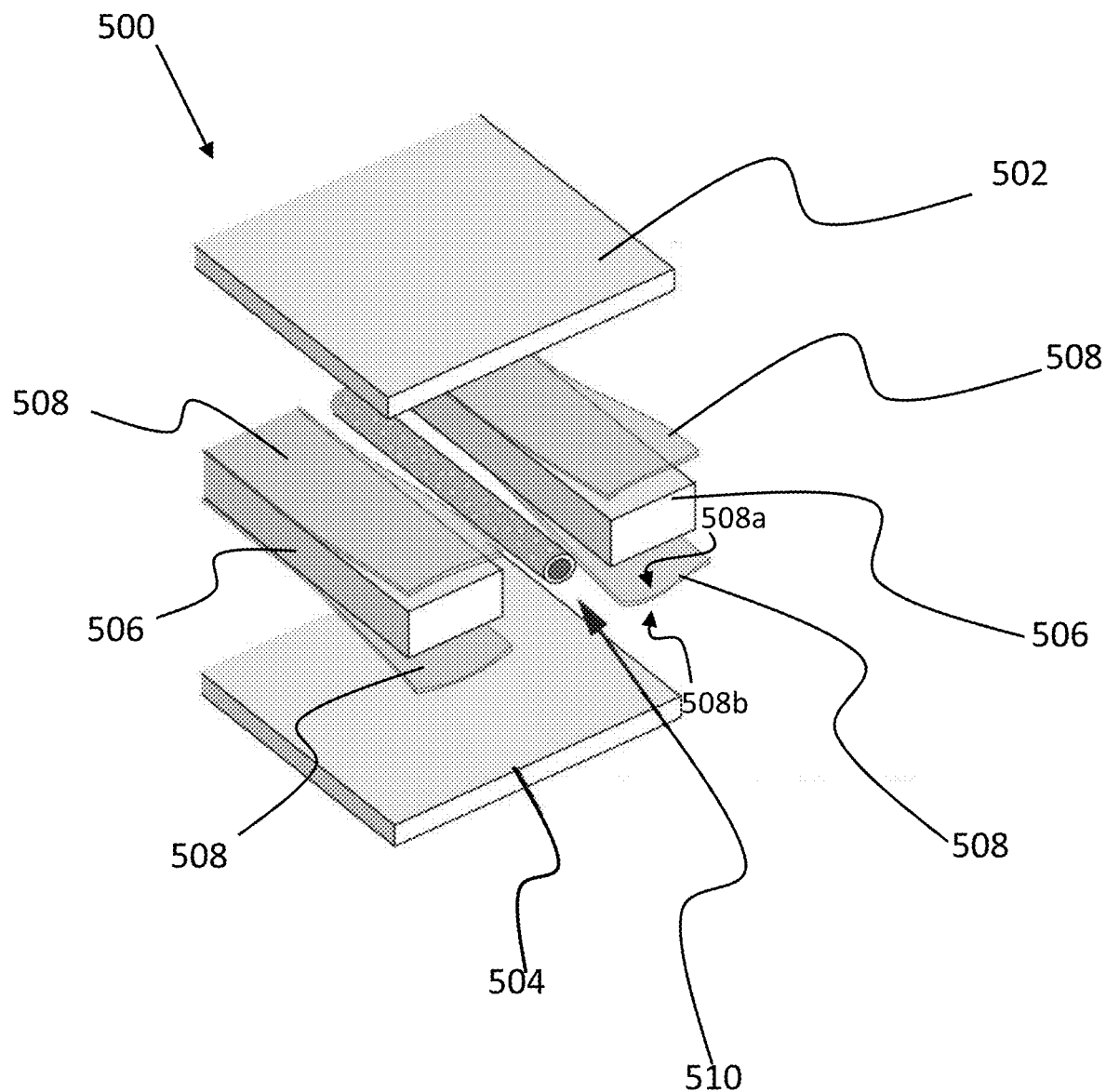
FIG. 5 is an exploded perspective view of another representative reversibly bonded device comprising a reversible bonding component.

Yet another example of a reversible bonded device is illustrated by FIG. 5. Device embodiment 500 of FIG. 5 can include a first substrate 502 and a second substrate 504 that are coupled through intermediate substrate components 506 and top and bottom layers of reversible bonding component 508, which comprises a first adhesive surface 508a and a second adhesive surface 508b. A hollow tube 510 can be positioned within channel 512 of reversible bonded device 500. The hollow tube 510 can be used for growing a biological sample within the reversible bonded device 500.

Figure 6:
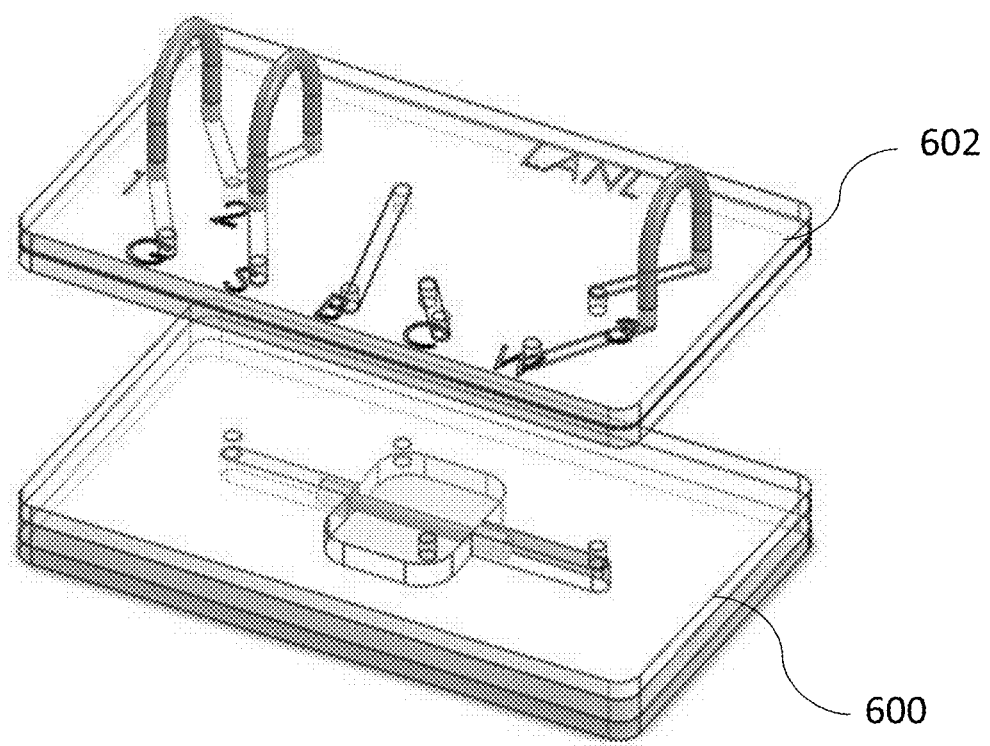
FIG. 6 is an exploded perspective view of a representative reversibly bonded device that is further coupled to a fluid management device using a reversible bonding component.
Figure 7:
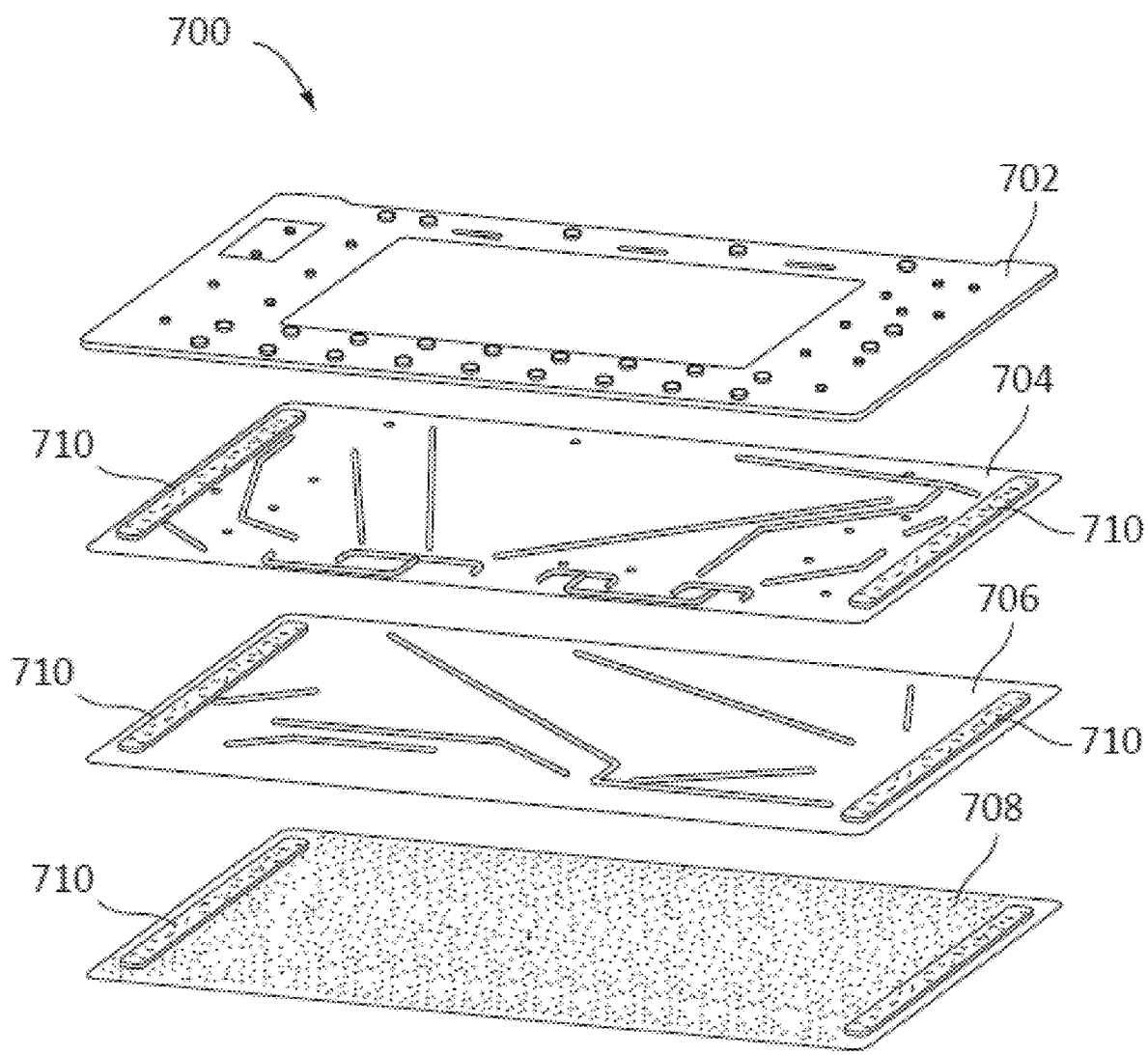
FIG. 7 is an exploded perspective view of a representative fluid management device comprising components that can be bonded together using a reversible bonding component.

In yet additional embodiments, the reversible bonding component can be used to couple a fluid management system to a device as illustrated in FIG. 6. The reversible bonding component can be added as a layer to either the surface of the device 600 that will interact with fluid management device 602, or it can be adhered to the bottom surface of fluid management device 602 so as to couple it to the top surface of device 600. The reversible bonding component 710 also can be used to couple substrates (e.g., 702, 704, 706, and 708) forming fluid management devices, such as device 700 illustrated in FIG. 7. In some embodiments, the reversible bonding component can be provided as adhesive strips 710 that are used to join the different substrates illustrated in FIG. 7.

Figure 10:
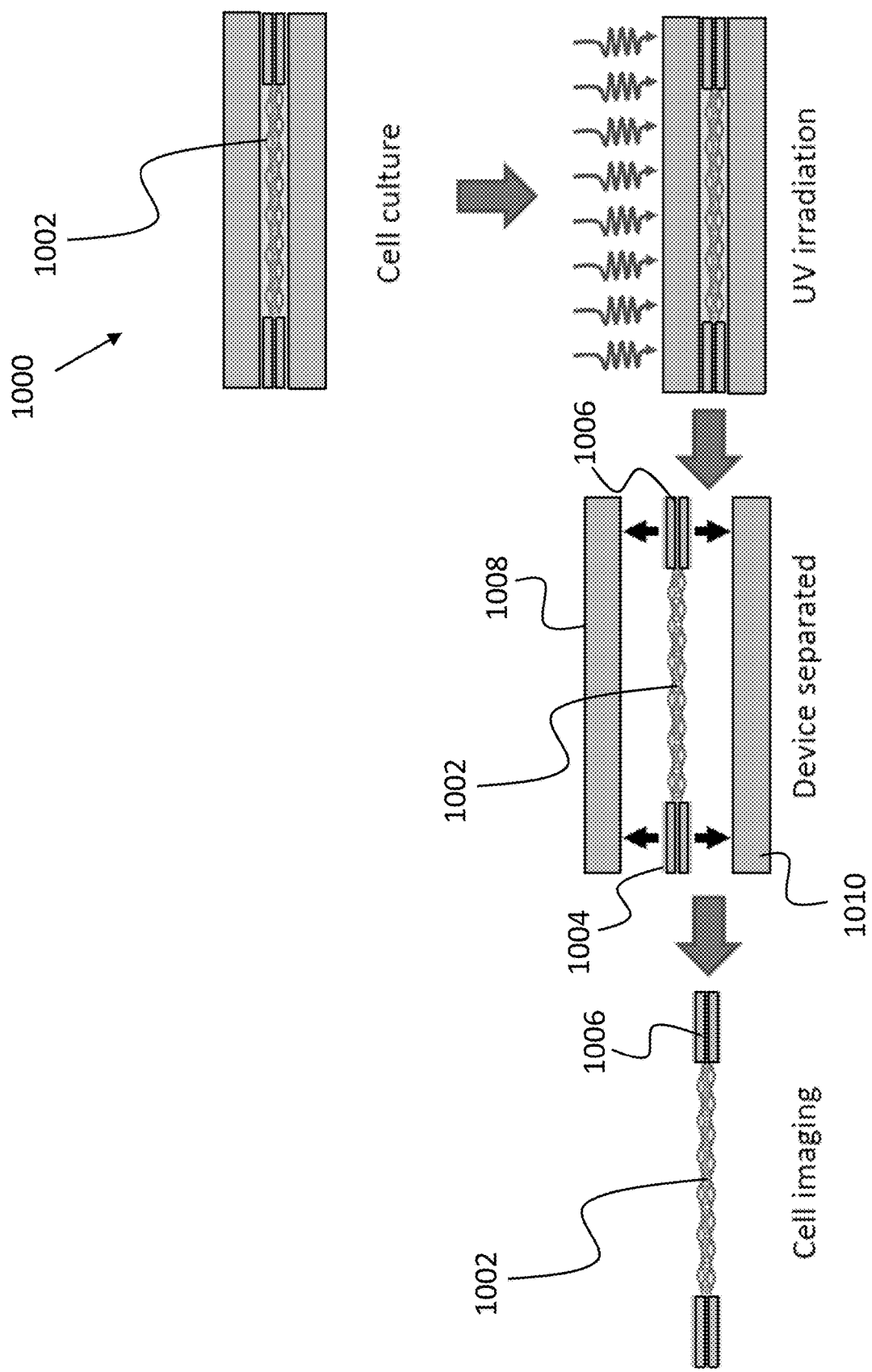
FIG. 10 is a schematic diagram illustrating a representative method of using the reversible bonding component to provide facile device deconstruction so that the internal sample can be characterized.

Another representative embodiment of a device described herein is illustrated in FIG. 10. With reference to FIG. 10, device 1000 comprises a first device component 1008 and a second device component 1010. Device 1000 further comprises a reversible bonding component 1004 that is coupled to the first device component 1008 and the second device component 1010. Device 1000 further comprises a biological sample 1002, which is contained within the constructed device using a membrane holder component 1006. As illustrated in FIG. 10, first device component 1008 and second device component 1010 are coupled through the reversible bonding component 1004 and because the reversible nature of the reversible bonding component, the first device component and the second device component can be reversibly coupled as can membrane holder component 1006.

IV. Methods of Making Devices

Disclosed herein are embodiments of methods for making devices comprising a reversible bonding component. While certain exemplary device embodiments are described in detail below, the methods disclosed herein can be applied to any device suitable for use with a reversible bonding component, including fluidic devices used for biological or non-biological applications. Non-biological applications may include those using devices that integrate membranes and utilize membrane extraction for follow-on application and analysis. Solely by way of example, platforms that grow or deposit nanostructures on a substrate under flow conditions can utilize the disclosed methods and device components. Substrates of such platforms can later be removed for characterization and collection of the nanostructures. Other technologies, such as fuel cells, filtration devices, catalytic reactors, and the like may be used in conjunction with the device components and/or methods disclosed herein.

In particular disclosed embodiments, the methods can comprise providing a first device component and coupling it to a reversible bonding component. Coupling can comprise exposing a surface of the device component to the reversible bonding component such that it completely covers or partially covers (e.g., covers less than 100% of the surface area of the device component) the surface of the device component. In some embodiments, the surface of the device component can be exposed to the reversible bonding component by manually positioning a layer of the reversible bonding component onto the surface or depositing a layer of the reversible bonding component onto the surface. Pressure can, but need not, be applied to the positioned/deposited layer of the reversible bonding component to secure it to the surface of the device component. Pressure can be applied by holding the components together with a clamp, lamination, and/or manually applying pressure.

In some embodiments, the method can further comprise modifying the reversible bonding component that has been adhered to the first device component. An exemplary modification can include patterning the reversible bonding component after it has been deposited onto the surface using a laser or manual cutting tool. In some embodiments, specific patterns can be cut into the reversible bonding component before or after it has been applied to the device component. This patterning capability is useful for device components that comprise particular channel configurations, inlets/outlets, and other structural features that must not be blocked or impeded by the adhesive layer. Patterns can be cut into the reversible bonding component manually or using an automated cutting tool, such as a laser. For example, the layer of the reversible bonding component can be patterned to expose certain portions of the device component that should not be covered with the reversible bonding component, such as fluidic channels, inlets, outlets, or other structural features formed into the device component. In yet additional embodiments, the reversible bonding component can be modified such that the exposed surface of the reversible bonding component (that is, the surface not adhered to the first device component) is converted to an adhesive surface. In some embodiments, a single-sided adhesive UV tape (or film) comprising an adhesive layer and a carrier layer can be converted to a double-sided adhesive UV tape (or film) by laminating the carrier layer of the single-sided adhesive UV tape (or film) with a layer of adhesive transfer tape to produce a double-sided adhesive UV tape (or film).

The methods can further comprise coupling a second device component with the first device component comprising the reversible bonding component. The second device component can be coupled to an exposed adhesive surface of the reversible bonding component in a manner similar to that described above for the first device component. The first and second device components are thereby coupled together through the reversible bonding component. This process can be repeated any number of times to couple together any number of device components. An exemplary device embodiment and an exemplary method embodiment are illustrated pictorially by FIGS. 8A and 8B. FIG. 8B is an exploded perspective view of an exemplary device embodiment 800 (FIG. 8A), which illustrates the various different device components and the order in which they can be arranged to provide a constructed device. According to the embodiment shown by FIG. 8B, a first substrate, such as upper channel substrate 802, can be coupled with a reversible bonding component layer 804, such as an adhesive UV tape. The reversible bonding component 804 used in the device embodiment illustrated in FIG. 8B can be patterned such that a channel pattern matching that of the upper channel substrate 802 is provided. The reversible bonding component 804 can further be coupled to a membrane-containing substrate 806, which comprises a membrane 808. Membrane-containing substrate 806 can in turn be coupled to a second reversible bonding component layer 810, which in turn is coupled to a lower channel layer 812. The substrates can be coupled in a step-wise process (e.g., upper channel substrate 802 to membrane-containing substrate 806, followed by membrane-containing substrate 806 to lower channel layer 812) or the substrates can be coupled simultaneously.

In some embodiments, devices can be constructed such that an internal sample is included in the device as it is constructed or such that a sample is introduced into the device after it has been constructed. Solely by way of example, an example of a device comprising an internal sample that is introduced into the device during the construction process can include a membrane-containing device wherein the membrane component comprises one or more biological material layers (e.g., one or more cell layers, tissue layers, and the like). Such a device can be constructed by coupling a reversible bonding component to a first substrate and then coupling a surface of the membrane, a portion of the surface of the membrane, or a surface of a membrane holder component that houses the membrane, to an exposed adhesive surface of the reversible bonding component. Alternatively, the reversible bonding component can be coupled to the membrane first (or a portion of the surface of the membrane or a membrane holder component) and then an exposed adhesive surface of the reversible bonding component can be coupled to the first substrate. Another layer of the reversible bonding component can then be coupled to the free surface of the membrane (or the membrane portion or the membrane holder) and a second substrate can be applied to an exposed adhesive surface of the reversible bonding component. Multiple layers of the same or different components can be stacked horizontally or vertically together to form the device.

Figure 9:
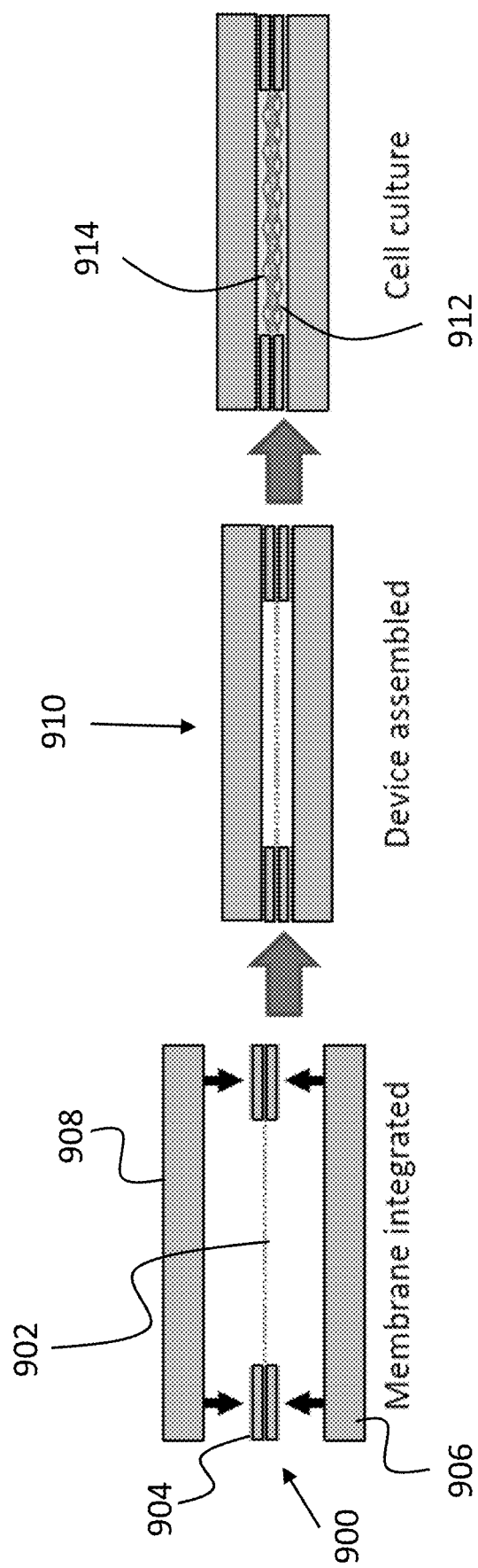
FIG. 9 is a schematic diagram illustrating a representative method of making a representative device embodiment utilizing a reversible bonding component.

In yet other embodiments, a device can be constructed as described above, but such that a sample is not associated with or attached to the membrane during device construction. Instead, the device can be constructed with a sample-free membrane positioned between two or more substrates (or positioned between two or more substrates and further held in place with a membrane holder). The sample can then be introduced into the device through one or more inlets fluidly coupled to one or more channels that further are in fluid communication with the membrane such that the sample is able to flow over or in proximity to the membrane and thereby associate with the membrane. An exemplary schematic diagram illustrating such a method is provided by FIG. 9. As shown in the embodiment of FIG. 9, a membrane holder component 900 can hold or house a membrane 902. The membrane holder component 900 comprises a layer of the reversible bonding component 904 on the exposed surfaces of the membrane holder component. Two substrates 906 and 908 can then be coupled to the reversible bonding component 904 to form assembled device 910. A sample, such as biological sample (e.g., a fluid containing cells or tissue), can be added into the assembled device so as to fill the space surrounding the membrane 902. In the embodiment illustrated in FIG. 9, cell cultures 912 and 914 (which can comprise the same or different cell species) are grown onto opposing surfaces of membrane 902.

V. Methods of Using Devices

Once the device is assembled, it can be used for its desired purpose until sample analysis is necessary. For example, if the device comprises an incubation chamber and/or components upon which cells and/or tissues are grown, the device can be used to grow layers of cells and/or tissues upon the component until enough cells/tissue is obtained for analysis/characterization and/or desired manipulations of the cells or tissue (such as exposure to one or more test compounds or conditions) is completed.

Whenever sample analysis is to be carried out, the device (or a portion of the device) can be exposed to an energy source capable of producing UV light. Upon exposure to UV light, the reversible bonding component's adhesive strength is reduced such that the components held together by the reversible bonding component can be easily separated. In some embodiments, the device can be exposed to an energy source that emits UV light for a particular time period, such as a time period ranging from at least one minute to 60 minutes or more, or 5 minutes to 60 minutes, or 10 minutes to 60 minutes, or 20 minutes to 60 minutes, or 30 minutes to 60 minutes. The length of time to which the reversible bonding component is exposed to UV light can vary depending on the identity of the reversible bonding component. For example, reversible bonding components exhibiting stronger adhesive properties can be exposed to UV light longer than those that exhibit weaker adhesive properties. In particular disclosed embodiments, the energy source can be any energy source capable of producing UV light, such as a UV lamp, a UV oven, a UV laser, or the like. UV light can be any light having wavelengths ranging from 400 nm to 10 nm, such as from 400 nm to greater than 320 nm, or from 400 nm to 350 nm.

In particular disclosed embodiments, a mask can be used to facilitate focusing UV exposure to a particular region of the device. For example, regions surrounding the sample can be exposed to UV light and the region where the sample is located can be covered with a suitable mask such that UV light does not pass through to the sample. Such embodiments provide the ability to focus UV light to desired portions of the device. This masking provides the ability to reduce adhesion strength of the reversible bonding component without exposing the sample to UV light that may deleteriously affect the sample; thus, components can be separated and sample integrity can be maintained (e.g., cell/tissue viability and physical structural characteristics are maintained). After UV exposure and reduction in adhesion strength, the sample can be characterized, such as by using confocal analysis, scanning electron microscopy, tunneling electron microscopy, and the like.

An exemplary method of using a reversible bonded device is illustrated in FIG. 10. As illustrated in FIG. 10, a constructed reversibly bonded device 1000 comprising a biological sample 1002 can be exposed to an energy source providing UV light. The adhesive strength of reversible bonding agent 1004 is weakened so that the device components to which it is coupled (e.g., membrane holder component 1006 and substrates 1008 and 1010) can be separated. The biological sample 1002 can then be analyzed/characterized without having to break the device.

VI. Examples

Example 1—Exemplary Lung Platform Device

In one example, a membrane (or plurality of membrane) is suspended and bonded on ~400 μm diameter apertures on a 10 μm thick polyester membrane substrate using a layer of adhesive UV plastic film from Ultron Systems, which is converted to a double-sided UV film by laminating a layer of adhesive transfer tape on the carrier layer of the single-sided adhesive UV film, with each planar sheet supporting 768 alveoli. Alveolar epithelial cells are inoculated on the airway side of the membrane component prior to system assembly. A stack of six transparent substrates are bonded to the airway side of the membrane component, wherein one or more of the substrates are bonded using a layer of the adhesive UV plastic film that is converted to a double-sided adhesive UV film using the method as described herein. Stacked substrates with increased thickness are connected with increased weight of inter-connected channels to allow ventilation of the alveolar surface using two reciprocating air pumps, one for alveoli simulating inhalation of $O_2$ and one for alveoli simulating exhalation of $CO_2$, with out-of-phase breathing to eliminate cyclic changes in pulmonary blood-surrogate volume. The resulting cyclic bubble-like alveolar expansion can increase membrane surface area and simulate mechanical stretching. The vascular side of the membrane component is overlaid with an adhesive UV plastic film-bonded stack of transparent substrates that produces a set of interconnected flow-through microchannels of growing dimensions, enabling uniform pressure and shear on the membrane material. The vascular side of the membrane material is seeded with pulmonary microvascular cells, which adhere to both the membrane material and the channel walls, and fluid shear forces will maintain cell polarization.

A bronchiolar device and alveolar device are integrated together to form lung organ system with relevant physiological functions to a native lung. In some embodiments, each bronchial hollow tube will connect with an alveolar unit; thus, five alveolar units connected with five bronchiolar hollow tubes can provide a total of 3840 alveoli and ~500 $mm^2$ surface area. Coupling the hollow tubes with co-cultured primary normal human bronchial epithelial (NHBE) cells and human lung microvascular endothelial (HLMVE) with the membrane material supporting human alveolar cells and HLMVEs in the same universal surrogate demonstrates the possibility to perform long term tissue culture in one platform.

Example 2—Cell Culture in Reversibly Bonded Device

Figure 8A:
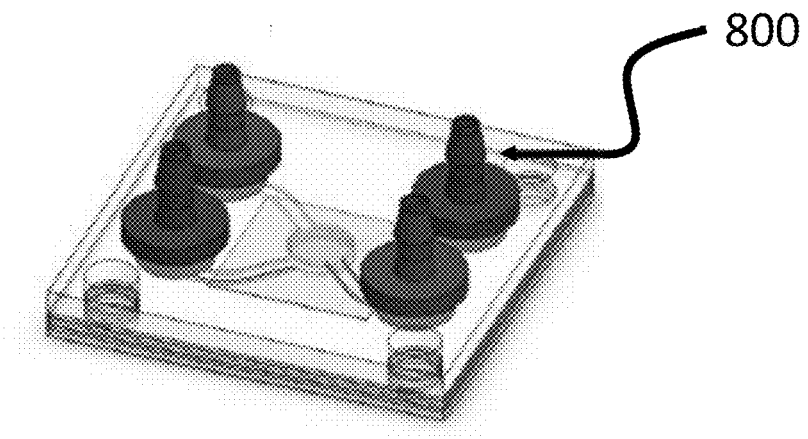
FIGS. 8A and 8B illustrate a device embodiment constructed using a reversible bonding component.
Figure 8B:
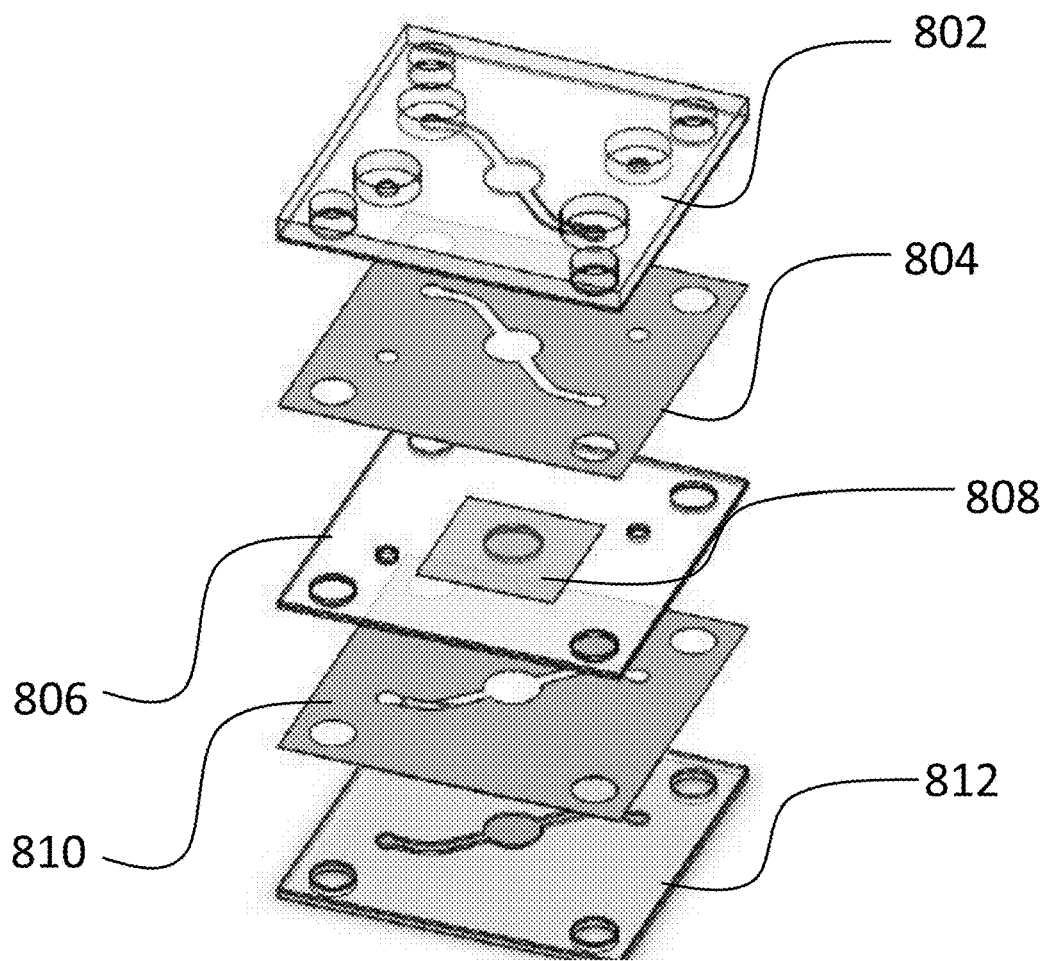
Figure 11A:
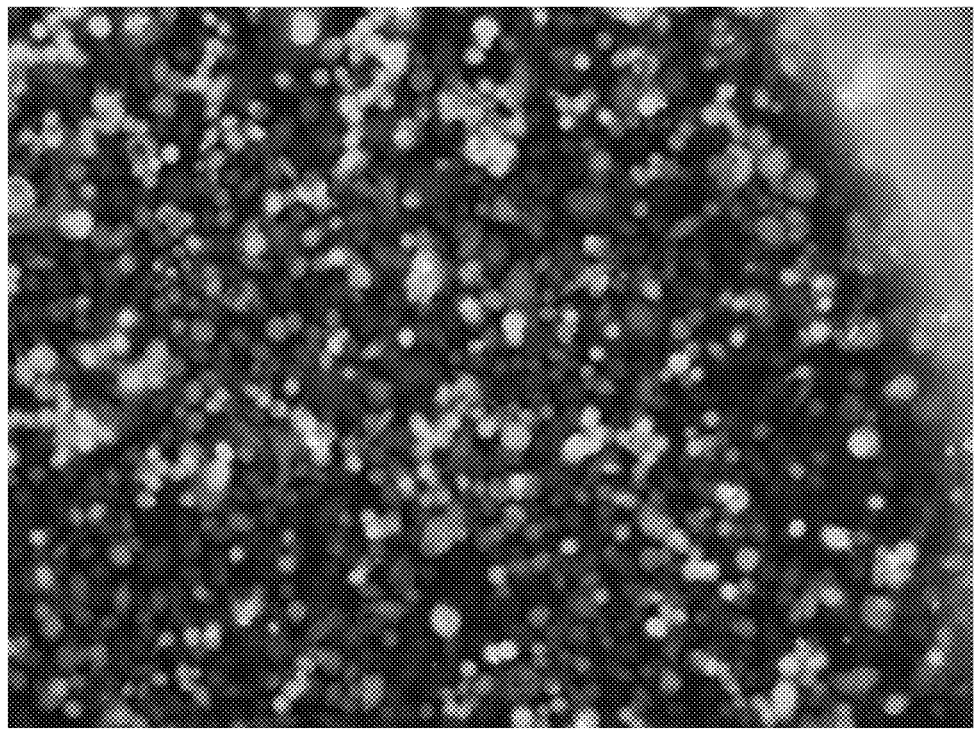
FIGS. 11A and 11B are images of cell cultures obtained from analyzing a sample extracted from a reversibly bonded device embodiment after 1 day (FIG. 11A) and after 5 days (FIG. 11B) of using the device.
Figure 11B:
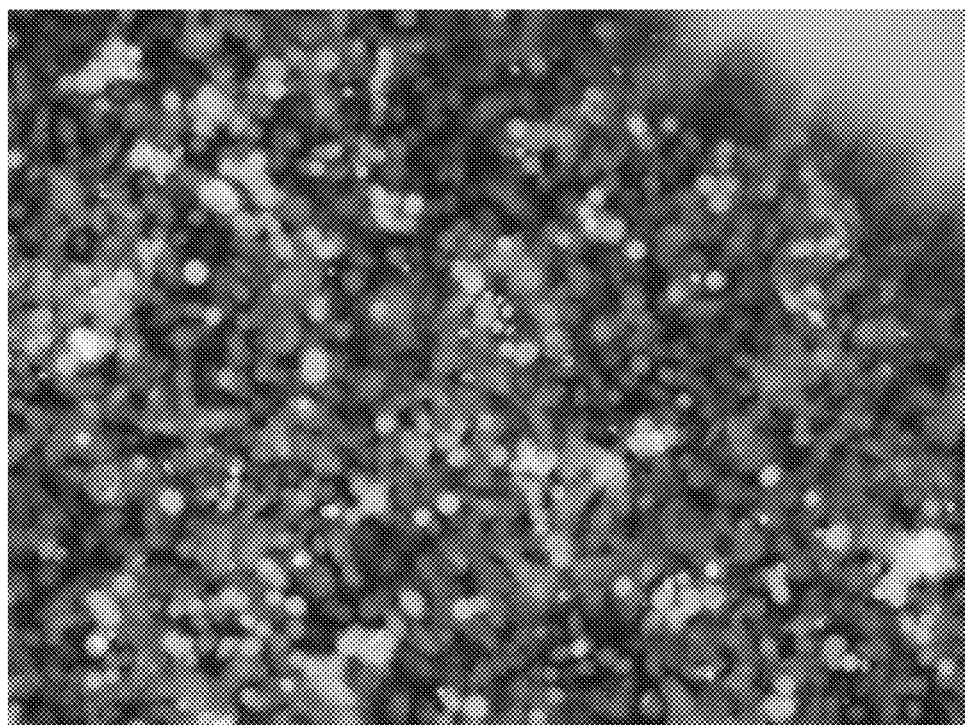
Figure 12:
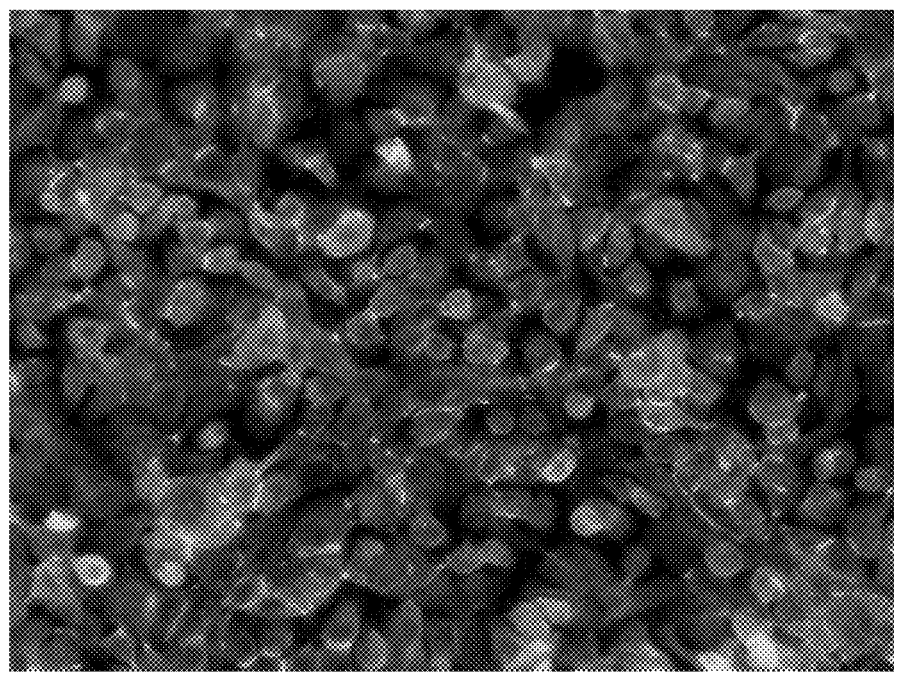
FIG. 12 is an image of a cell culture obtained from analyzing a sample with tight junction staining after the sample has been extracted from a reversibly bonded device embodiment after 5 days.

In another example, the device illustrated in FIGS. 8A and 8B was fabricated using an embodiment of the fabrication methods disclosed herein and sterilized using an alcohol wash. The membrane component of the device was then seeded with cells. The cells were allowed to grow for 3-5 days. After the growth period, the device was exposed to UV light for 5-10 minutes. Following irradiation, it was possible to remove the membrane with cells from the device. The cells on the membranes were then stained with commercially available dye and a fluorescent microscope was used to take the images illustrated in FIGS. 11A, 11B, and 12.

VII. Overview of Several Embodiments

In some embodiments, the reversibly bonded device disclosed herein can comprise a first device component; a second device component; a reversible bonding component coupled to the first device component, the second device component, or both, wherein the first device component and the second device component are reversibly coupled by the reversible bonding component. In some embodiments, the reversibly bonded device can further comprise a biological sample contained within the reversible bonded device.

In some embodiments, the reversible bonding component comprises a first adhesive surface and a second adhesive surface.

In any or all of the above embodiments, the device can further comprise a membrane component, a hollow tube component, a membrane holder component, a second reversible bonding component, or a combination thereof.

In any or all of the above embodiments, the membrane component and/or the hollow tube component can be positioned between the first device component and the second device component.

In any or all of the above embodiments, a portion of first adhesive surface of the reversible bonding component can be adhered to a portion of a surface of the first device component and a portion of the second adhesive surface of the reversible bonding component can be adhered to a portion of a surface of the second device component, the membrane component, or the membrane holder component.

In any or all of the above embodiments, the reversible bonding component can be patterned to match one or more patterns of the first device component and/or the second device component.

In any or all of the above embodiments, the one or more patterns of the first device component and/or the second device components include fluidic channels, inlets, outlets, and combinations thereof.

In any or all of the above embodiments, the reversible bonding component can be an adhesive UV tape, adhesive UV film, or an adhesive UV composition.

In any or all of the above embodiments, the biological sample comprises cells, tissues, or combinations thereof.

In any or all of the above embodiments, the biological sample is associated with or attached to the membrane, the hollow tube, or both.

In any or all of the above embodiments, the first device component and/or the second device component is a transparent substrate.

In some embodiments, the reversibly bonded device comprises a first transparent substrate; a second transparent substrate; a membrane positioned between the first transparent substrate and the second transparent substrate; a membrane holder component coupled to the membrane and positioned between the first transparent substrate and the second transparent substrate; a first UV tape layer adhered to a first surface of the membrane holder component and a surface of the first transparent substrate; and a second UV tape layer adhered to a second surface of the membrane holder component and a surface of the second transparent substrate.

In any or all of the above embodiments, the device can further comprise one or more cell or tissue layers associated with or attached to the membrane.

Also disclosed herein are embodiments of a method of making a reversibly bonded device, comprising: adhering a reversible bonding component to a surface of a first device component; adhering the reversible bonding component to a surface of a second device component; and coupling the first device component to the second device component through the reversible bonding component.

In some embodiments, the method further comprises introducing a biological sample into the device or growing a biological sample in the device.

Also disclosed herein are embodiments of a method of using a reversibly bonded device, comprising introducing a biological sample into the reversibly bonded device or growing a biological sample in the reversibly bonded device; exposing the reversibly bonded device to a light source. In some embodiments, the method can further comprise deconstructing the reversibly bonded device to access the biological sample for analysis.

In some embodiments, deconstructing the reversibly bonded device comprises physically separating the first device component from the second device component without damaging the first device component, the second device component, or the biological sample.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of using a reversibly bonded device, comprising:

providing a reversibly bonded device;

introducing a biological sample into a region of the reversibly bonded device or growing a biological sample in a region of the reversibly bonded device;

covering the region of the reversibly bonded device that contains the biological sample with a mask that prevents UV light from reaching the region of the reversibly bonded device that contains the biological sample; and exposing the reversibly bonded device to a UV light source to reverse bonding of a reversibly adhesive UV tape that is used to adhere portions of the reversibly bonded device.

2. The method of claim 1, wherein the reversibly bonded device comprises a first device component, a second device component, and the reversible adhesive UV tape, wherein the reversible adhesive UV tape is coupled to the first device component, the second device component, or both, and wherein the first device component and the second device component are reversibly coupled by the reversible adhesive UV tape.

3. The method of claim 1, wherein the method further comprises deconstructing the reversibly bonded device to access the biological sample for analysis.

4. The method of claim 3, wherein deconstructing the reversibly bonded device comprises physically separating the first device component from the second device component without damaging the first device component, the second device component, or the biological sample.

5. The method of claim 1, wherein the biological sample comprises cells, tissues, or combinations thereof.

6. The method of claim 2, wherein the reversible adhesive UV tape comprises a first adhesive surface and a second adhesive surface.

7. The method of claim 2, wherein the reversibly bonded device further comprises a membrane component, a hollow tube component, a membrane holder component, a second layer of a reversible adhesive UV tape, or a combination thereof.

8. The method of claim 7, wherein the biological sample is associated with or attached to the membrane component, the hollow tube, or both.

9. The method of claim 8, wherein the membrane component and/or the hollow tube component is positioned between the first device component and the second device component.

10. The method of claim 9, wherein a portion of the first adhesive surface of the reversible adhesive UV tape is adhered to a portion of a surface of the first device component and a portion of the second adhesive surface of the reversible adhesive UV tape is adhered to a portion of a surface of the second device component, the membrane component, or the membrane holder component.

11. The method of claim 2, wherein the reversible adhesive UV tape is patterned to match one or more patterns of the first device component and/or the second device component.

12. The method of claim 11, wherein the one or more patterns of the first device component and/or the second device components include fluidic channels, inlets, outlets, and combinations thereof.

13. The method of claim 2, wherein the first device component and/or the second device component is a transparent substrate.

14. The method of claim 2, wherein the reversibly bonded device further comprises:

an additional layer of the reversible adhesive UV tape;

a membrane component positioned between the first device component and the second device component and associated with the biological sample;

a membrane holder component coupled to the membrane component and positioned between the first device component and the second device component, and wherein each of the first device component and the second device component comprises a transparent substrate and wherein the layer of the reversible adhesive UV tape is adhered to a first surface of the membrane holder component and a surface of the first device component and the additional layer of the reversible adhesive UV tape is adhered to a second surface of the membrane holder component and a surface of the second device component and wherein the mask covers the region of the reversibly bonded device that contains the membrane component that is associated with the biological sample.

15. The method of claim 14, further comprising one or more cell or tissue layers associated with or attached to the membrane.

\* \* \* \* \*